United States Patent
Junge et al.

(10) Patent No.: US 8,918,227 B2
(45) Date of Patent: Dec. 23, 2014

(54) DEVICE AND METHOD FOR DETERMINING A VIGILANCE STATE

(75) Inventors: Mirko Junge, Cramme (DE); Maria Staubach, Wolfsburg (DE)

(73) Assignee: Volkswagen AG, Wolfsburg (DE)

( * ) Notice: Subject to any disclaimer, the term of this patent is extended or adjusted under 35 U.S.C. 154(b) by 0 days.

(21) Appl. No.: 13/516,940

(22) PCT Filed: Nov. 23, 2010

(86) PCT No.: PCT/EP2010/007090
§ 371 (c)(1),
(2), (4) Date: Sep. 27, 2012

(87) PCT Pub. No.: WO2011/072794
PCT Pub. Date: Jun. 23, 2011

(65) Prior Publication Data
US 2013/0015010 A1 Jan. 17, 2013

(30) Foreign Application Priority Data
Dec. 16, 2009 (DE) .......................... 10 2009 058 459

(51) Int. Cl.
B60K 28/02 (2006.01)
A61B 5/18 (2006.01)
A61B 5/16 (2006.01)
G08B 21/06 (2006.01)
B60K 28/06 (2006.01)

(52) U.S. Cl.
CPC . *A61B 5/162* (2013.01); *A61B 5/18* (2013.01); *A61B 5/165* (2013.01); *G08B 21/06* (2013.01); *B60K 28/066* (2013.01)
USPC .............. 700/306; 180/272; 180/280; 701/42

(58) Field of Classification Search
CPC .......... B08B 23/00; A61B 5/165; A61B 5/18; B60K 28/066
USPC .......... 700/306; 340/576, 575; 180/272, 281, 180/280; 701/42
See application file for complete search history.

(56) References Cited

U.S. PATENT DOCUMENTS 6,661,345 B1 * 12/2003 Bevan et al. .................. 340/575
8,199,018 B2 * 6/2012 Shigetou .................... 340/573.1
(Continued)

FOREIGN PATENT DOCUMENTS

| CN | 101296657 | 10/2008 |
|---|---|---|
| EP | 1 257 202 | 11/2002 |
| EP | 1 929 950 | 6/2008 |

OTHER PUBLICATIONS

International Search Report, issued in corresponding International Application No. PCT/EP2010/007090.

*Primary Examiner* — Karen Beck
(74) *Attorney, Agent, or Firm* — Kenyon & Kenyon LLP

(57) ABSTRACT

In a method and a device for determining a vigilance state of a motor vehicle driver,
 a noise signal is generated and a supplementary torque as a function of the noise signal is applied to a steering assembly,
 a reaction signal of the vehicle driver is determined, and
 the vigilance state is determined from a time characteristic of the noise signal and a time characteristic of the reaction signal, at least one parameter of a parameterized transfer function from noise signal to reaction signal is determined, and the vigilance state is determined as a function of an absolute value of the at least one parameter and/or as a function of a relative change of the at least one parameter with regard to at least one earlier parameter, the at least one earlier parameter having been determined at an earlier instant in time.

19 Claims, 2 Drawing Sheets

(56) References Cited

U.S. PATENT DOCUMENTS

| | | |
|---|---|---|
| 2003/0011481 A1* | 1/2003 | Bjorkman .................... 340/576 |
| 2004/0054452 A1 | 3/2004 | Bjorkman |
| 2008/0221401 A1* | 9/2008 | Derchak et al. .............. 600/301 |
| 2010/0109881 A1* | 5/2010 | Eskandarian et al. ........ 340/575 |
| 2011/0043350 A1* | 2/2011 | Ben David .................... 340/441 |
| 2011/0319721 A1* | 12/2011 | Hamaguchi ................... 600/300 |
| 2013/0015010 A1* | 1/2013 | Junge et al. ................... 180/272 |

* cited by examiner

DEVICE AND METHOD FOR DETERMINING A VIGILANCE STATE

FIELD OF THE INVENTION

The invention relates to a method and a device for determining a vigilance state of a motor vehicle driver.

BACKGROUND INFORMATION

In an effort to improve road safety by detecting inattentiveness or fatigue of a vehicle driver, methods are implemented for determining a vigilance state, i.e., an alertness state, of the vehicle driver. This method endeavors to improve road safety by detecting unusual behavior of the vehicle driver and making it known. The unusual behavior may be due to inattention or fatigue, for instance. Fatigue frequently affects the reaction times of the vehicle driver such that reflexes or reactions to particular driving situations take place more slowly, with a delay, and/or less assuredly.

European Published Patent Application No. 1 257 202 describes a method for transmitting a pulse to a vehicle during travel. The pulse is initiated by one or more trigger(s), and the driver usually responds to the pulse spontaneously and subconsciously. The pulse is transmitted to the steering assembly (or to another component with which the driver is normally in contact). Furthermore, a response of the driver is detected by one or multiple sensor(s), such as a steering angle sensor, torque sensor, acceleration force sensor or eye movement sensor. In addition, European Published Patent Application No. 1 257 202 describes that the pulse and the response are compared in order to infer presence of mind of the driver, the presence of mind being inversely proportional to the difference between the pulse and the response. In this regard European Published Patent Application No. 1 257 202 states that the presence of mind of the vehicle driver is detectable in two different ways. In a first alternative, a difference between the pulse and the response is added up and integrated over a specific period of time. The smaller the result of the integration, the better the vehicle driver is able to respond to interruptions. In a second alternative, an amplitude of a centrifugal force in a lateral direction is analyzed. In addition, a reaction time of the driver is able to be determined in the form of a time difference between two different instants, a first instant T1 resulting when the pulse exceeds a predefined threshold value, and a second instant resulting when the reaction exceeds a second predefined threshold value. This has the disadvantage that the threshold-based detection of the first and second instants for determining the reaction time is susceptible to noise. Measuring noise, as it is generated by the afore-mentioned sensors, for instance, may falsify the detection of a response time of the vehicle driver.

SUMMARY

Example embodiments of the present invention provide a method and a device for determining a vigilance state of a motor vehicle driver by which an improved, in particular more reliable, determination of the vigilance state is possible.

Provided is a method for determining a vigilance state of a motor vehicle driver. A noise signal is generated in the method, and a supplementary torque, which is a function of the noise signal, is applied to a steering assembly, in particular to a steering column of a motor vehicle. The noise signal is an artificially produced signal. The noise signal preferably is a zero-mean signal. In addition, the noise signal preferably is a random signal or a pseudo-random signal. Moreover, the noise signal preferably has small amplitudes, small amplitudes not affecting a steering behavior and a driving behavior of the motor vehicle, or affecting them only negligibly. For example, the noise signal may be generated by a steering control unit of the, for instance, electromechanical steering assembly. Of course, the noise signal is also able to be generated by other control units, which preferably are situated inside the motor vehicle. Various alternatives exist for applying the supplementary torque to the steering column. In the case of an electromechanical steering assembly, in which a servomotor applies a supplementary torque to a steering rack or the steering column, the supplementary torque may be generated with the aid of the servomotor. For this purpose, the noise signal may be added to a setpoint value of the servo torque. The setpoint value of the servo torque is the value that the servomotor, for instance, is to apply to the steering rack. As an alternative, the supplementary torque may also be generated by a unit for producing a supplementary torque and be applied to the steering column directly or indirectly, e.g., with the aid of a transmission. It is possible, for example, that a steering assembly includes an additional servomotor, and that the additional servomotor is used exclusively for generating the supplementary torque. Depending on the individual case, it is also possible to use hydraulic actuators of a servo-steering assembly for generating the supplementary torque.

In this case, the supplementary torque may be applied to the steering column either directly or indirectly. An indirect application means that the supplementary torque is also applicable to an element of the steering assembly that is mechanically connected to the steering column. For example, the supplementary torque may be applied to the steering rack to which steerable wheels of the motor vehicles are connected. In this case the steering rack is mechanically coupled to the steering column, primarily in order to transmit steering motions of the vehicle driver to the steering rack. Because of the mechanical coupling, the supplementary torque is transmitted from the steering rack to the steering column and is able to be haptically perceived by the vehicle driver, for instance via a steering wheel. However, the supplementary torque may also be applied to the steering system, such that a change in the vehicle movement actually does occur, but no haptic feedback is noticeable at the steering wheel via the steering column.

Moreover, a time characteristic of the noise signal is stored. A time characteristic of the noise signal may be stored in a memory unit, for example, and/or in the steering control unit.

The vehicle driver will then haptically perceive the supplementary torque, which is a function of the noise signal and applied to the steering column, and then attempt to compensate it by an automatic, i.e., subconscious, reaction. The same holds true if the supplementary torque produces only a change in the vehicle movement, without haptic feedback. Here, too, the vehicle driver will automatically attempt to compensate for the change. In this case a response of the vehicle driver for compensating the supplementary torque is reflected in a reaction signal. This reaction signal of the vehicle driver is determined as described herein. The reaction signal may be ascertained from at least one state variable from the group of manual torque, yaw rate, steering angle, steering angle velocity, rotor position of the servomotor and other state quantities. The reaction signal is preferably determined as the manual torque the vehicle driver applies to the steering column via a steering wheel. In this case the manual torque is detectable by a steering torque sensor. A time characteristic of the reaction signal is also stored in a memory unit and/or in the steering control unit, for instance.

The reaction signal thus determined includes two components. A first component is generated from a sum of the steering motions, the sum of the steering motions being made up of a driving task of the vehicle driver. For example, the driving task consists of navigation components, e.g., steering maneuvers for following a scheduled route. Furthermore, the driving task includes steering maneuvers which, for instance, result from different maneuvers of the vehicle such as passing maneuvers. In addition, the driving task includes steering maneuvers for stabilizing the vehicle, e.g., when driving over a road bump. As a second component, the reaction signal includes steering motions of the vehicle driver for the purpose of compensating the supplementary torque.

The second component does not have to be separated from the first component in terms of signaling in order to determine a vigilance state of the vehicle driver. In particular, there is no need to use predefined threshold values, for example, to determine the point as of which a reaction signal is composed exclusively of components for compensating the supplementary torque.

However, filtering of the reaction signal is possible in order to improve the signal quality of the reaction signal. The filtering, however, need not separate the first and the second component of the reaction signal.

In example embodiments of the present invention, the vigilance state of the vehicle driver is determined from a time characteristic of the noise signal and a time characteristic of the reaction signal. Toward this end, at least one parameter of a parameterized transfer function from noise signal to reaction signal is determined. The parameterized transfer function at least partially models a dynamic steering behavior of the vehicle driver. Linear transfer functions or non-linear transfer functions are possible as transfer function. The at least one parameter of the parameterized transfer function may be determined with the aid of a method for identifying a linear or non-linear transfer function.

The vigilance state of the vehicle driver is then determined as a function of an absolute value of the at least one parameter and/or as a function of a relative change in the at least one parameter in relation to at least one earlier parameter. The at least one earlier parameter is determined at an earlier instant by the method described herein. If the vigilance state is determined as a function of an absolute value of the at least one parameter, then it is possible that the at least one parameter may not exceed, or drop below, a predefined threshold value. A suitable predefined threshold value may be chosen, for instance as a function of a vehicle model. However, the vigilance state is preferably determined by evaluating the relative change in the at least one parameter. A change in the vigilance state may be detected if a relative change of the at least one parameter exceeds a predefined threshold value, e.g., 10 percent. The at least one earlier parameter may be determined at an earlier instant which precedes the current instant by a predefined time period such as, for instance, 20 or 30 minutes.

Depending on the absolute and/or relative change in the at least one parameter, a critical or non-critical vigilance state of the vehicle driver is able to be determined. If a critical vigilance state of the vehicle driver is determined, then a warning signal, e.g., an optical or acoustic warning signal, can be produced or a rest recommendation be generated.

The method described herein may result in a simpler and more reliable determination of a vigilance state, a vigilance state, in particular, being able to be determined more independently of measuring noise.

The at least one parameter of the parameterized transfer function may be determined with the aid of a cross-correlation of the noise signal with the reaction signal. For instance, a transfer function is able to be determined using $$R_{YX}(t) = R_{XX}(t) * h(t) \qquad \text{Formula 1}$$

In this case, $R_{YX}(t)$ denotes a cross-correlation function of the noise signal with the reaction signal, and $R_{XX}(t)$ denotes an autocorrelation function of the noise signal. Furthermore, h(t) denotes the pulse response of a linear, time-invariant transfer function, $R_{YX}(t)$ resulting from a convolution of $R_{XX}(t)$ and the pulse response. The use of pulse response h(t) advantageously makes it possible to determine the transfer function in a reliable and easily implementable manner. Using standardized methods for system identification, e.g., a least squares method, the at least one parameter of the parameterized transfer function is able to be determined with the aid of the pulse response h(t).

The at least one parameter of the parameterized transfer function may be determined with the aid of an autocorrelation of the noise signal and an autocorrelation of the reaction signal. The following holds true for a linear, time-invariant transfer function:

$$R_{YY}(t) = R_{XX}(t) * h(t) * h(-t) \qquad \text{Formula 2}$$

Here, $R_{YY}(t)$ denotes the autocorrelation function of the reaction signal, $R_{XX}(t)$ denotes the autocorrelation function of the noise signal, and h(t) once again denotes the pulse response. This example embodiment, too, may advantageously be used to determine the transfer function in a reliable and easily implementable manner.

According to known transfer rules, the relationships represented in formulas 1 and 2 may also be transformed from a time range into a frequency range. The searched-for transfer function in the frequency range then results from a corresponding multiplication of the spectral power density functions $S_{XX}(\omega)$, $S_{XY}(\omega)$, $S_{YY}(\omega)$ with the transfer function $H(\omega)$ in the frequency range.

Moreover, it is possible to evaluate a correlation coefficient of the cross-correlation function $R_{XY}(t)$. In this case it is possible to calculate the cross-correlation coefficient also for a cross-correlation of the reaction signal with a noise signal that precedes the reaction signal by a predefined time difference, and it is also possible to carry out a calculation for multiple time differences. If multiple time differences are evaluated, then the time difference between the noise and the reaction signal that corresponds to the maximum correlation coefficient, for instance, corresponds to a delay time of the vehicle driver. In this case a vigilance state may be determined as a function of the time difference and/or the absolute value of the correlation coefficient and/or a change in the correlation coefficient in relation to a correlation coefficient that had been determined earlier.

The parameterized transfer function may be a linear and/or time-invariant transfer function. The parameterized transfer function preferably is a linear and/or time-invariant transfer function. The linear and/or time-invariant transfer function usually is an approximation of the normally non-linear dynamic steering behavior of the vehicle driver. Using the linear and/or time-invariant transfer function, the dynamic steering behavior of the vehicle driver around a working point of the non-linear systems is modeled as approximately linear. For this purpose monitoring periods, i.e., periods for which the vigilance state is determined, are shortened such that temporal changes of the system need not be taken into account explicitly when modeling the transfer function. This advantageously results in a computationally simple determination of the at least one parameter of the parameterized transfer function, without undesired inaccuracies in the modeling of the transfer function affecting the determination of the vigilance state.

The parameterized transfer function may model at least one dead-time element. In this connection, a dead-time element in the frequency range, especially in the Laplace range, may be represented as $$G_1(s) = e^{-sT_s} \quad \text{Formula 3}$$

$T_s$ denotes the dead time, and dead time $T_s$ denotes a time period between a change at the system input and a response at the system output. Dead time $T_s$ may advantageously represent a response time of the vehicle driver. Dead time $T_s$ must therefore be considered a parameter of a parameterized transfer function.

The parameterized transfer function may represent at least one low-pass element. A low-pass element in the frequency range, in particular in the Laplace range, may be described by $$G_2(s) = K/(1+Ts) \quad \text{Formula 4}$$

K denoting an amplification factor, and T, a time constant of the low-pass element. This advantageously makes it possible to describe a dynamic steering behavior of the motor vehicle driver well enough to determine the vigilance state. A forcefulness of the reaction of the vehicle driver, in particular, is able to be ascertained via a determination of amplification factor K. Time constant T provides information about a speed of the steering behavior. The parameterized transfer function preferably represents a dead-time element and a low-pass element. The parameterized transfer function may also include additional, more complex transfer elements, e.g., transfer elements of the second order, proportional elements, integration elements, and differentiating elements. In addition, the parameterized transfer function may represent feedback of the output signal, in this case, the reaction signal, with regard to the input signal, in this case, the noise signal. This has the advantage that the control a person actually has over motive sequences in the steering behavior are able to be described even better. By representing the feedback, it is possible to take the particular fact into account that the vehicle driver generally does not execute any forceful steering reactions.

The at least one parameter may be determined continuously, at regular time intervals or at selected points in time. The continuous determination of the at least one parameter advantageously provides a continuous determination of the vigilance state of the vehicle driver. For continuous monitoring, time intervals of a predefined duration of the noise signal and the response signal, for example, may be used for determining the at least one parameter. For instance, for a continuous determination of the at least one parameter, it is possible to utilize time characteristics of the noise signal and the reaction signal within a predefined time interval of, for instance, 40 seconds prior to the actual instant. It may also be the case that the time interval has a shorter or longer duration and/or does not end directly before the actual instant, but ends a predefined time period prior to the actual instant. Ascertaining the at least one parameter at regular time intervals advantageously reduces the computational work in connection with the determination of the at least one parameter. In this context it is for possible, for example, that the at least one parameter is determined every minute, every five minutes, every 10 minutes, every 15 minutes, or every 30 minutes. Other time intervals for a regular determination, or no continuous determination, of the at least one parameter are possible as well. Determining the at least one parameter at selected instants advantageously results in a further reduction of the computational work. It is possible that a determination of the at least one parameter takes place following a braking operation, following a steering operation, when a previously defined vehicle speed is exceeded or not attained, or as a function of additional dynamic vehicle processes, for example.

The noise signal may be a low-frequency and/or zero-mean noise signal. A person driving a vehicle normally is able to detect and compensate only low-frequency signals. A low-frequency signal is understood to refer to a signal having an upper limit frequency of maximally 20 Hz, the upper limit frequency preferably lying between 2 and 10 Hz. This has the advantage that the noise signal is particularly suitable for determining the at least one parameter, and thus the vigilance state of the vehicle driver.

In a non-critical vigilance state, at least one method for training cognitive information-processing processes of the vehicle driver may be activated. As an alternative or cumulatively, a warning signal may be generated in a critical vigilance state. This advantageously makes it possible to improve the information processing functions within a vehicle guidance framework by training, in particular if older vehicle drivers are involved. Especially deficits in the parallel processing of information, that is to say, in so-called divided attention cases are able to be compensated. The training keeps the driver active, and thereby prevents him from slipping into a critical vigilance state under monotonous conditions.

For example, an application of cognitive training programs may occur on monotonous road segments that pose low cognitive demands, and/or during rides with low steering demands. For example, travel and/or road segments making low cognitive demands are defined in the following manner:
  road segments that are shorter than 300 km,
  low traffic volume,
  optimal illumination and weather conditions, especially travel in daylight, travel without fog, without rain, without snow, or without sun glare,
  simple road demands, e.g., very few bends and/or road construction sites.

Systems may be provided for detecting suitable road segments for an application of cognitive training programs.

A further prerequisite for the application of cognitive training programs is that the described method for determining the vigilance state ascertains an average to excellent vigilance of the vehicle driver.

Furthermore, the driver may be able to activate and deactivate the application of cognitive training programs. The application of cognitive training programs may furthermore be interruptable, especially when unexpected or difficult driving situations arise, which require the vehicle driver's undivided attention.

For example, cognitive training programs may be provided in the following manner:
  Reaction task in response to signals, e.g., acoustic and/or visual signals. For acoustic signals, a simultaneous distribution of the vehicle driver's cognitive resources to the driving task and the training task is advantageously possible. When reacting to visual signals, the visual signals must relate to a currently existing traffic situation, since no split of cognitive resources is possible. For example, a reaction task may consist of responding to a particular vehicle class or particular driving maneuvers of the own car or of other cars.
  reasoning tasks via voice-operated operator interfaces,
  tasks in connection with the respective driving task, e.g., when passing a vehicle, while attending to all other demands (glance over the shoulder, acceleration, etc.).

It is especially preferred if the cognitive training programs trigger playful ambitions of the vehicle driver. This advantageously induces the vehicle driver to perform the tasks of a cognitive training program repeatedly.

Furthermore provided is a device for steering a motor vehicle, the steering assembly including at least one unit for generating a noise signal, and at least one unit for applying to the steering assembly at least one supplementary torque as a function of the noise signal, in particular to a steering column of the motor vehicle.

In addition, the steering assembly includes at least one unit for determining a reaction signal of a vehicle driver, and at least one unit for system identification. With the aid of the provided device, at least one of the afore-described methods is able to be implemented.

Further features and aspects of example embodiments of the present invention are explained in greater detail below with reference to the appended Figures.

DETAILED DESCRIPTION

Figure 1:
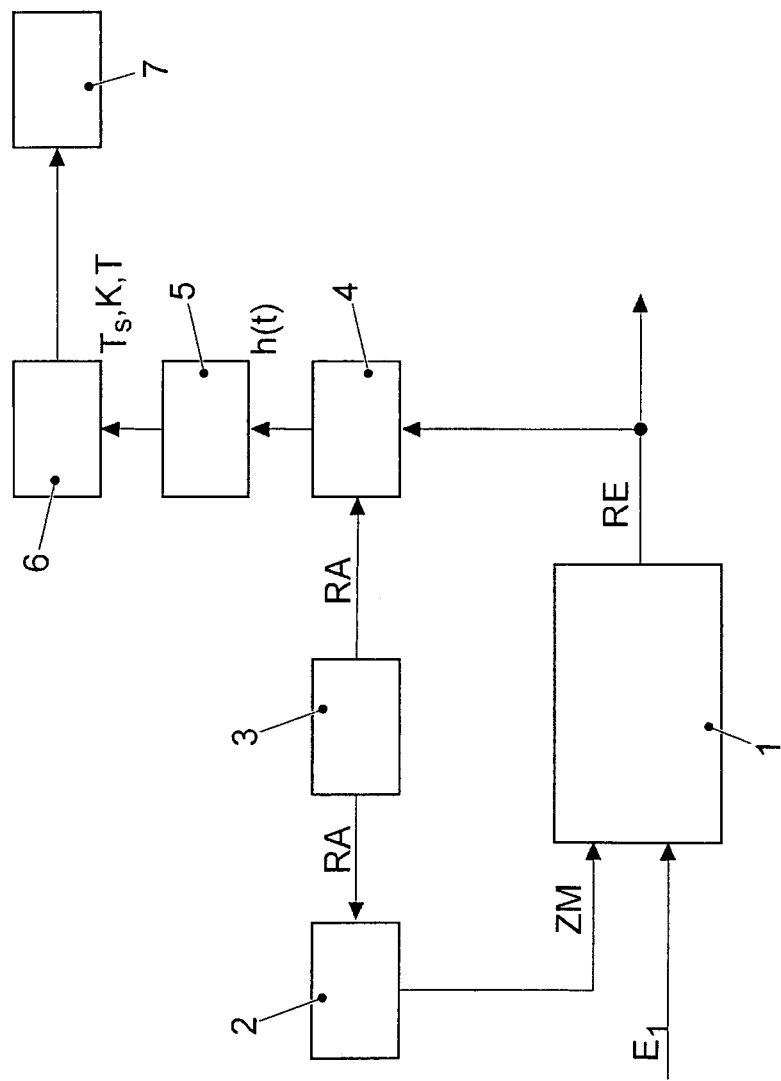
FIG. 1 is a schematic signal characteristic of a method for determining a vigilance state.

In the following text, identical reference numerals denote elements having the same or similar technical properties.

FIG. 1 shows a schematic signal characteristic in a method for determining a vigilance state of a vehicle driver 1. Vehicle driver 1 detects two input signals. A first input signal E1 is composed of a sum of steering motions resulting from a driving task. Steering motions in this case result from a navigation wish of vehicle driver 1, from performed driving maneuvers, such as a passing maneuver, and from steering motions for the purpose of stabilizing the vehicle. A second input signal for vehicle driver 1 is a supplementary torque ZM applied to steering column 10 shown in FIG. 2. Supplementary torque ZM is produced by a unit 2 for generating supplementary torque ZM. Unit 2 for generating supplementary torque ZM, for instance, may be servomotor 13 shown in FIG. 2. Unit 2 for generating supplementary torque ZM generates supplementary torque ZM as a function of noise signal RA. Noise signal RA is generated by a unit 3 for generating a noise signal RA. Vehicle driver 1 generates a reaction signal RE as a function of first input signal E1 and supplementary torque ZM. Noise signal RA and reaction signal RE are transmitted via data link to a unit 4 for correlation. Unit 4 for correlation determines a pulse response h(t), e.g., by a cross-correlation of noise signal RA with reaction signal RE, and an autocorrelation of noise signal RA. A unit 5 for system identification uses pulse response h(t) and a predefined parameterized transfer function to determine the parameters of the transfer function. The transfer function in this case may represent a dead-time element and a low-pass element, for example. As parameters, the transfer function includes a dead time $T_s$, an amplification factor K, and a time constant T. A unit 6 for determining the vigilance state determines the vigilance state of vehicle driver 1 as a function of an absolute and/or relative change in dead time $T_s$, amplification factor K, and time constant T. In the event that unit 6 for detecting the vigilance state detects a critical vigilance state of vehicle driver 1, unit 6 for determining the vigilance state is able to activate a unit 7 for warning vehicle driver 1. In such a case, unit 7 for warning vehicle driver 1 generates an acoustic warning signal, for example.

Figure 2:
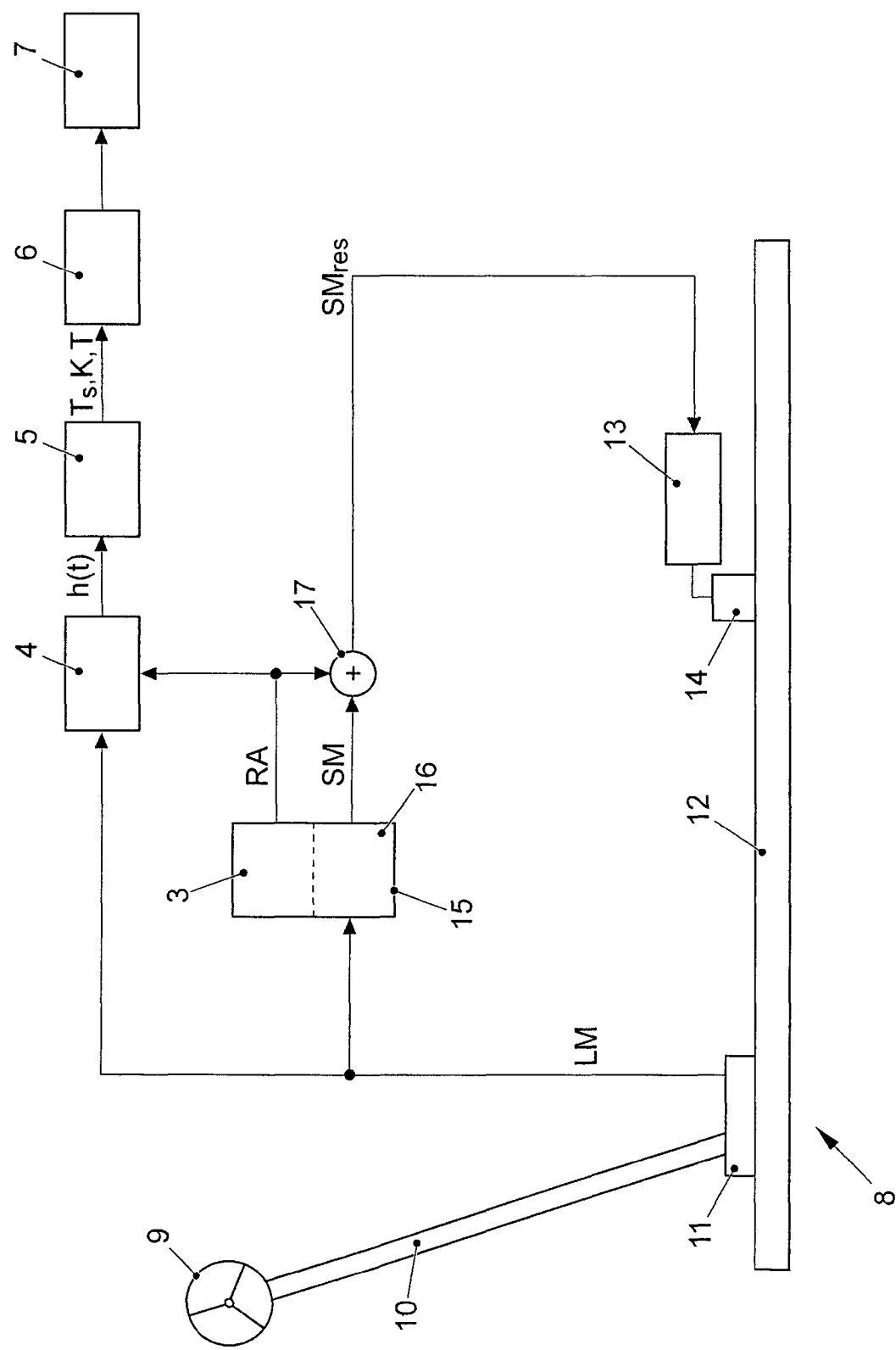
FIG. 2 is a schematic block diagram of a steering assembly of a motor vehicle.

FIG. 2 illustrates a schematic block diagram of a device 8 for steering a motor vehicle (not shown). Device 8 includes a steering wheel 9, a steering column 10, which is mechanically coupled to steering wheel 9, a sensor 11 for detecting a steering torque LM, a steering rack 12, and a servomotor 13, which is coupled to steering rack 12 via a transmission 14. In addition, device 8 includes a steering control unit 15. Steering control unit 15 encompasses unit 3 for producing a noise signal RA shown in FIG. 1. Steering control unit 15 also includes a unit 16 for calculating a servo moment SM. Unit 16 for calculating a servo moment SM calculates a servo moment SM from steering torque LM by a calculation rule. Detected steering torque LM also includes a manual torque applied to steering column 10 by vehicle driver 1 by steering wheel 9. An adder unit 17 adds noise signal RA generated by unit 3 for generating a noise signal RA to servo moment SM. Servo moment $SM_{res}$ resulting from this calculation is used as setpoint value for servomotor 13. Servomotor 13 generates a torque as a function of resulting servo torque $SM_{res}$ which it applies to steering rack 12 with the aid of transmission 14. In other words, servomotor 13 serves as unit 2 for applying a supplementary torque ZM (see FIG. 1) in this case, supplementary torque ZM depending on the time characteristic of noise signal RA. Supplementary torque ZM as a function of noise signal RA is transmitted to steering column 10 via steering rack 12. Sensor 11 for detecting steering torque LM then detects a manual torque that results from steering motions of vehicle driver 1, which, for one, consists of the previously described steering motions and, for another, are used for compensating supplementary torque ZM. Steering torque LM and noise signal RA produced by unit 3 for generating a noise signal RA are transmitted via data link to a unit 4 for correlation. Similar to the method for determining a vigilance state of a vehicle driver 1 described in connection with FIG. 1, unit 4 for correlation calculates a pulse response h(t). A unit 5 for system identification identifies a dead time $T_s$, an amplification factor K, and a time constant T. Depending on detected parameters $T_s$, K, T, a unit 6 for determining the vigilance state determines a critical or non-critical vigilance state and, if warranted, is able to activate a unit 7 for warning vehicle driver 1. In the example embodiment shown in FIG. 2, sensor 11 for detecting the steering torque corresponds to the at least one unit for determining a reaction signal RA of vehicle driver 1.

List Of Reference Characters
1 vehicle driver
2 unit for producing a supplementary torque
3 unit for generating a noise signal
4 unit for correlation
5 unit for system identification
6 unit for determining a vigilance state
7 unit for warning a vehicle driver
8 device for steering a motor vehicle
9 steering wheel
10 steering column
11 sensor for detecting a steering torque
12 steering rack
13 servomotor
14 transmission
15 steering control unit
16 unit for calculating a servo moment
E1 first input signal
ZM supplementary torque
RA noise signal RE reaction signal
h(t) pulse response
$T_s$ dead time
K amplification factor
T time constant
SM servo moment
$SM_{res}$ resulting servo moment
LM steering torque

What is claimed is:

1. A method for determining a vigilance state of a vehicle driver, comprising:
   generating a noise signal;
   applying a supplementary torque to a steering assembly as a function of the noise signal;
   determining a reaction signal of the vehicle driver;
   determining at least one parameter of a parameterized transfer function from the noise signal to the reaction signal; and
   determining the vigilance state (a) from a time characteristic of the noise signal and a time characteristic of the reaction signal and (b) as a function of at least one of (i) an absolute value of the at least one parameter and/or (ii) a relative change of the at least one parameter with regard to at least one earlier parameter determined at an earlier instant in time;
   wherein the parameterized transfer function includes a linear transfer function and/or time-invariant transfer function.

2. The method according to claim 1, wherein the at least one parameter of the parameterized transfer function is determined by a cross-correlation of the noise signal with the reaction signal.

3. The method according to claim 1, wherein the at least one parameter of the parameterized transfer function is determined by an autocorrelation of the noise signal and/or an auto-correlation of the reaction signal.

4. The method according to claim 1, wherein the parameterized transfer function represents at least one dead-time element.

5. The method according to claim 1, wherein the parameterized transfer function represents at least one low-pass element.

6. The method according to claim 1, wherein the at least one parameter is determined continuously, at regular time intervals, or at selected points in time.

7. The method according to claim 1, wherein the noise signal includes a low-frequency noise signal and/or a zero-mean noise signal.

8. The method according to claim 1, wherein in a non-critical vigilance state, at least one method for training cognitive information processing processes of the vehicle driver is activated, and/or a warning signal is generated in case of a critical vigilance state.

9. The method according to claim 1, wherein the method is performed by a device including:
   the steering assembly;
   at least one unit adapted to generate the noise signal;
   at least one unit adapted to apply the at least one supplementary torque to the steering assembly as a function of the at least one noise signal;
   at least one unit adapted to determine the reaction signal of the vehicle driver; and
   at least one unit adapted for system identification and adapted to determine the at least one parameter of a parameterized transfer function of the noise signal to the reaction signal.

10. A device for steering a motor vehicle, comprising:
    a steering assembly;
    at least one unit adapted to generate a noise signal;
    at least one unit adapted to apply at least one supplementary torque to the steering assembly as a function of at least one noise signal;
    at least one unit adapted to determine a reaction signal of a vehicle driver; and
    at least one unit adapted for system identification and adapted to determine at least one parameter of a parameterized transfer function of the noise signal to the reaction signal;
    wherein the parameterized transfer function includes a linear transfer function and/or time-invariant transfer function.

11. The device according to claim 10, wherein the device is adapted to perform a method for determining a vigilance state of the vehicle driver, including:
    generating the noise signal;
    applying the supplementary torque to the steering assembly as a function of the noise signal;
    determining the reaction signal of the vehicle driver;
    determining the at least one parameter of a parameterized transfer function from the noise signal to the reaction signal; and
    determining the vigilance state (a) from a time characteristic of the noise signal and a time characteristic of the reaction signal and (b) as a function of at least one of (i) an absolute value of the at least one parameter and/or (ii) a relative change of the at least one parameter with regard to at least one earlier parameter determined at an earlier instant in time.

12. A method for determining a vigilance state of a vehicle driver, comprising:
    generating a noise signal;
    applying a supplementary torque to a steering assembly as a function of the noise signal;
    determining a reaction signal of the vehicle driver;
    determining at least one parameter of a parameterized transfer function from the noise signal to the reaction signal; and
    determining the vigilance state (a) from a time characteristic of the noise signal and a time characteristic of the reaction signal and (b) as a function of at least one of (i) an absolute value of the at least one parameter and/or (ii) a relative change of the at least one parameter with regard to at least one earlier parameter determined at an earlier instant in time;
    wherein the method is performed by a device including:
      the steering assembly;
      at least one unit adapted to generate the noise signal;
      at least one unit adapted to apply the at least one supplementary torque to the steering assembly as a function of the at least one noise signal;
      at least one unit adapted to determine the reaction signal of the vehicle driver; and
      at least one unit adapted for system identification and adapted to determine the at least one parameter of a parameterized transfer function of the noise signal to the reaction signal;
    wherein the parameterized transfer function includes a linear transfer function and/or time-invariant transfer function.

13. A device for steering a motor vehicle, comprising:
    a steering assembly;
    at least one unit adapted to generate a noise signal;

at least one unit adapted to apply at least one supplementary torque to the steering assembly as a function of at least one noise signal;

at least one unit adapted to determine a reaction signal of a vehicle driver; and at least one unit adapted for system identification and adapted to determine at least one parameter of a parameterized transfer function of the noise signal to the reaction signal;

wherein the device is adapted to perform a method for determining a vigilance state of the vehicle driver, including:

generating the noise signal;

applying the supplementary torque to the steering assembly as a function of the noise signal;

determining the reaction signal of the vehicle driver;

determining the at least one parameter of a parameterized transfer function from the noise signal to the reaction signal; and determining the vigilance state (a) from a time characteristic of the noise signal and a time characteristic of the reaction signal and (b) as a function of at least one of (i) an absolute value of the at least one parameter and/or (ii) a relative change of the at least one parameter with regard to at least one earlier parameter determined at an earlier instant in time;

wherein the parameterized transfer function includes a linear transfer function and/or time-invariant transfer function.

14. The method according to claim 1, wherein the noise signal is an artificially produced signal.

15. The method according to claim 1, wherein the noise signal includes a random signal and/or a pseudo-random signal.

16. The method according to claim 1, wherein the noise signal does not substantially affect a steering behavior and/or a driving behavior of the vehicle driver.

17. A method for determining a vigilance state of a vehicle driver, comprising:

generating a noise signal;

applying a supplementary torque to a steering assembly as a function of the noise signal;

determining a reaction signal of the vehicle driver;

determining at least one parameter of a parameterized transfer function from the noise signal to the reaction signal; and determining the vigilance state (a) from a time characteristic of the noise signal and a time characteristic of the reaction signal and (b) as a function of at least one of (i) an absolute value of the at least one parameter and/or (ii) a relative change of the at least one parameter with regard to at least one earlier parameter determined at an earlier instant in time;

wherein the noise signal is generated by a control unit of the steering assembly.

18. A method for determining a vigilance state of a vehicle driver, comprising:

generating a noise signal;

applying a supplementary torque to a steering assembly as a function of the noise signal;

determining a reaction signal of the vehicle driver;

determining at least one parameter of a parameterized transfer function from the noise signal to the reaction signal; and determining the vigilance state (a) from a time characteristic of the noise signal and a time characteristic of the reaction signal and (b) as a function of at least one of (i) an absolute value of the at least one parameter and/or (ii) a relative change of the at least one parameter with regard to at least one earlier parameter determined at an earlier instant in time;

wherein the noise signal is added to a setpoint value of the supplementary torque.

19. A method for determining a vigilance state of a vehicle driver, comprising:

generating a noise signal;

applying a supplementary torque to a steering assembly as a function of the noise signal;

determining a reaction signal of the vehicle driver;

determining at least one parameter of a parameterized transfer function from the noise signal to the reaction signal; and determining the vigilance state (a) from a time characteristic of the noise signal and a time characteristic of the reaction signal and (b) as a function of at least one of (i) an absolute value of the at least one parameter and/or (ii) a relative change of the at least one parameter with regard to at least one earlier parameter determined at an earlier instant in time;

wherein the supplementary torque is generated via a servomotor.

* * * * *